US010450265B2

(12) United States Patent
Dai et al.

(10) Patent No.: US 10,450,265 B2
(45) Date of Patent: Oct. 22, 2019

(54) METHOD FOR PRODUCING AMIDES OR POLYAMIDES BY USING AROMATIC CARBAMATES BY WAY OF ISOCYANATES AS PRECURSORS THROUGH CATALYZED THERMAL PROCESSES AND METHOD FOR PRODUCING AROMATIC CARBAMATE PRECURSORS FROM AROMATIC AMINES

(71) Applicant: Great Eastern Resins Industrial Co., Ltd., Taichung (TW)

(72) Inventors: Shenghong A. Dai, Taichung (TW); Ching Hsuan Lin, Taichung (TW); Jung-Yang Yang, Taichung (TW)

(73) Assignee: Great Eastern Resins Industrial Co., Ltd., Taichung (TW)

( * ) Notice: Subject to any disclaimer, the term of this patent is extended or adjusted under 35 U.S.C. 154(b) by 126 days.

(21) Appl. No.: 15/653,591

(22) Filed: Jul. 19, 2017

(65) Prior Publication Data

US 2018/0186731 A1    Jul. 5, 2018

(30) Foreign Application Priority Data

Dec. 29, 2016   (TW) .............................. 105143958 A (51) Int. Cl.

| *C07C 269/04* | (2006.01) |
|---|---|
| *C08G 69/00* | (2006.01) |
| *C07C 263/04* | (2006.01) |
| *C07C 267/00* | (2006.01) |
| *C07C 273/18* | (2006.01) |
| *C07C 231/10* | (2006.01) |
| *C08G 69/04* | (2006.01) |
| *C08G 69/26* | (2006.01) |
| *C08G 69/28* | (2006.01) |
| *C08G 69/32* | (2006.01) |

(52) U.S. Cl.
CPC .......... *C07C 269/04* (2013.01); *C07C 231/10* (2013.01); *C07C 263/04* (2013.01); *C07C 267/00* (2013.01); *C07C 273/1809* (2013.01); *C08G 69/00* (2013.01); *C08G 69/04* (2013.01); *C08G 69/26* (2013.01); *C08G 69/28* (2013.01); *C08G 69/32* (2013.01)

(58) Field of Classification Search
CPC ............................. C07C 231/00; C07C 269/04
See application file for complete search history.

(56) References Cited

U.S. PATENT DOCUMENTS

| 3,620,664 A | 11/1971 | Hobart et al. |
|---|---|---|
| 6,143,917 A | 11/2000 | Harada et al. |
| 6,781,010 B1 | 8/2004 | Mason |
| 2007/0282078 A1* | 12/2007 | Dai ...................... C07D 209/48 525/424 |

FOREIGN PATENT DOCUMENTS

| EP | 2275405 A1 | 1/2011 |
|---|---|---|
| JP | 2009074035 A | 4/2009 |
| JP | 2015120878 A | 7/2015 |
| TW | 200800867 A | 1/2008 |
| TW | 200906912 A | 2/2009 |
| TW | 200948760 A | 12/2009 |
| TW | 201313664 A | 4/2013 |

OTHER PUBLICATIONS

Mikolajczyk et al., Recent Developments in the Carbodiimide Chemistry, *Tetrahedron*, vol. 37, Issue 2, pp. 233-284 (1981).
Neumann et al., "The Preparation of Carbodiimides from Isocyanates", *Angew. Chem. Internat. Edit.*, vol. 1, No. 12, pp. 621-625 (1962).
Yamazaki et al., "The Reaction of Diphenyl Carbonate with Amines and its Application to Polymer Synthesis", *Journal of Polymer Science: Polymer Chemistry Edition*, vol. 17, pp. 835-841 (1979).
Chen, A-L., "Well-Defined Polyamide Syntheis from Diisocyanates and Diacids Involving Hindered Carbodiimide Intermediates", Macromoledules, 2011, vol. 44, No. 1, pp. 46-59.

\* cited by examiner

*Primary Examiner* — Kuo Liang Peng
(74) *Attorney, Agent, or Firm* — Drinker Biddle & Reath LLP (57) ABSTRACT

The present invention is directed to a process for preparing amides or polyamides by replacing isocyanate starting materials of a catalyzed thermal reaction with aromatic carbamates. Through the catalyzed thermal process involving a non-isocyanate precursor of the present invention, efficiency for producing amides or polyamides can be significantly improved, and the impure side products produced from a side reaction of isocyanate can be greatly curtailed. Hence, amides or polyamides of high purity and yield can be achieved. The invention also relates to a process for preparing aromatic carbamates, the new non-isocyanate precursors for amides or polyamides.

13 Claims, 6 Drawing Sheets

METHOD FOR PRODUCING AMIDES OR POLYAMIDES BY USING AROMATIC CARBAMATES BY WAY OF ISOCYANATES AS PRECURSORS THROUGH CATALYZED THERMAL PROCESSES AND METHOD FOR PRODUCING AROMATIC CARBAMATE PRECURSORS FROM AROMATIC AMINES

CROSS-REFERENCE TO RELATED APPLICATIONS

This application claims priority to Taiwanese Application No. 105143958, filed Dec. 29, 2016, which is incorporated herein by reference in its entirety.

FIELD OF THE INVENTION

The present invention relates to a method for preparing an amide or polyamide by replacing an isocyanate starting material of a catalyzed thermal reaction with an aromatic carbamate. The present invention also relates to a method for preparing an aromatic carbamate precursor from an aromatic amine.

BACKGROUND OF THE INVENTION

Because of the good tensile strength, toughness, impact resistance, gas barrier property, and weather and chemical resistance, polyamide (also known as Nylon) is widely used in various industries, such as the automotive, textile and electrical industries, and can be used in a broad range of new applications. For example, polyamide filament can be made into socks, underwear lining, sweatshirts, and ski raincoats. The fabric produced by blending the staple polyamide fiber with cotton and viscose fibers can be imparted with good wear resistance and strength. Polyamide fibers may also be used in velcro, carpet, cord fabric, conveyor belts, fishing net, cable, canvas roofs or the like. Aromatic polyamides are particularly heat-resistant and fire-resistant, and are applicable to special fire-protection and high-tech materials.

In regard to the methods for producing amides or polyamides, TW 200800867 and TW 200906912 developed a new polycondensation synthesis mechanism, i.e., sequential self-repetitive reaction, in which a diisocyanate and a diacid monomer are thermally condensed in the presence of a CDI catalyst at an elevated temperature to produce a polyamide. The sequential self-repetitive reaction at least comprises the following three repetitive and sequential reaction steps:

(1) in the presence of a CDI catalyst, such as 1,3-dimethyl-3-phospolene oxide (DMPO) or 3-methyl-phenyl-3-phosphorene-1-oxide (MPPO), condensing two molecules of an isocyanate, to synthesize an aromatic carbodiimide (CDI);

(2) adding a carboxylic acid to the aromatic carbodiimide, to form a reaction intermediate N-acyl urea; and (3) thermally cracking the N-acyl urea, to produce a polyamide and one molecule of isocyanate, where the isocyanate produced in Step (3) proceeds to Step (1) so as to conduct a new round of sequential self-repetitive reaction for synthesizing the polyamide, until all the isocyanate is completely consumed.

Isocyanates are highly reactive so they easily react with water to produce urea. In addition, isocyanates have other disadvantages such as difficulty in storage, high toxicity and tendency for side reactions. Therefore, isocyanates have limitations and defects when used in a sequential self-repetitive catalyzed thermal reaction. Moreover, the inventors of the present invention have found that conventional high-polarity polymerization solvents containing tertiary amine nitrogen, such as anhydrous N-methyl-2-pyrrolidone (NMP), N,N-dimethylacetamide (DMAc), and N,N-dimethylformamide (DMF), that are commonly used for preparing amides or polyamides are prone to react with the isocyanate to produce by-products. It is further found that in most cases, non-linear and non-amide by-products could be formed and result in a bimodal distribution of the prepared polyamide when analyzed for the molecular weight distribution by GPC. The above result shows that the prepared polyamide is accompanied by obvious by-products, so the physical and mechanical properties of the prepared product are less desirable and more inclining to be degraded. Accordingly, to solve the technical problem associated with isocyanate being prone to react with water, the present invention suggests using an aromatic carbamate, rather than an isocyanate, as an alternative starting material of a catalyzed thermal reaction. By using an aromatic carbamate, water could be first removed during the initial thermal treatment. The de-watered aromatic carbamate is then decomposed into an isocyanate at an elevated temperature. Hence, the side reaction is suppressed so as to improve the process conditions. In this way, in comparison with the prior art process, a polyamide produced according to the method of the present invention could have improved physical and mechanical properties.

Another object of the present invention is to provide an improved method for preparing an aromatic carbamate that is used as a stable material for producing isocyanate in the present invention. At the time of the priority date of the present invention, the phosgene process is still a major process in the industrial production of isocyanate. However, the phosgene process incurs strong toxicity. For example, a large amount of by-product hydrogen chloride is produced during a phosgene process. In addition, since the product has relatively high chlorine content, the production equipment is expensive and requires frequent maintenance. Furthermore, the by-product hydrogen chloride produced during the phosgene process is a corrosive compound that easily reacts with an amine compound to form a solid amine salt. Although the amine salt may be further reacted with phosgene to produce the isocyanate, the reaction rate is slow and the reaction needs to be conducted at a high temperature. Therefore, once the solid amine salt is deposited in a pipeline, public safety incidents may be caused due to the obstruction of the corroded pipeline. As such, considering the environmental protection and public safety issues encountered during a phosgene process, there is still a need for an efficient and green method to replace such process.

The preparation of an aromatic carbamate through the diphenyl carbonate (DPC) process was first proposed by N. Yamazaki in 1979 (N. Yamazaki, T. Iguchi, Journal of Polymer Science: Polymer Chemistry Edition, 17, 835, 1979). However, the selectivity and yield of the aromatic carbamate product prepared according to the process are at most 80%, and the reaction rate is quite slow, so when the reaction temperature is elevated, the content of the by-product urea is increased accordingly. U.S. Pat. Nos. 6,143,917, 6,781,010 and EP 2275405 also developed processes for preparing an aromatic carbamate with diphenyl carbonate (DPC), so as to produce an isocyanate. Considering the insufficient selectivity and yield of the aromatic carbamate prepared according to conventional diphenyl carbonate processes, another objective of the present invention is to increase the yield of the aromatic carbamate to 90% or higher, preferably 95% or higher, and particularly preferably 98% or higher, by replacing the prior art with a novel combination of catalysts.

SUMMARY OF THE INVENTION

In a conventional catalyzed thermal reaction regarding an aromatic isocyanate and a carboxylic acid, a target product is synthesized in the presence of a CDI catalyst, such as a phospholene oxide. Since a reaction intermediate N-acyl urea would be produced during a catalyzed thermal reaction (that is, an intermediate product is produced through the reaction of a carbodiimide with a carboxylic acid), the N-acyl urea is cracked at a high temperature, to produce a polyamide, that is, the product, and halved isocyanate. The isocyanate further undergoes the catalyzed thermal reaction with the carboxylic acid.

However, to solve the defect of the isocyanate being prone to side reaction with water, an aromatic carbamate is used as a raw material in the present invention, which is thermally cracked to release the isocyanate (a transient intermediate, i.e., a precursor) at an adjusted temperature and production rate, during which the water in the reaction solution can be removed in advance. In the present invention, the aromatic carbamate is also preferably used to replace all the aromatic isocyanates involved in the catalyzed thermal reaction, and the defect mentioned previously can be greatly improved through a catalyzed thermal reaction route exemplified by the preparation of an amide shown below:

where Ar denotes an aryl group having 6 to 17 carbon atoms and preferably phenyl, pyridinyl, or a 4- to 6-membered heterocyclic group containing 1 to 3 nitrogen, sulfur, or oxygen atoms and substituted with 1 to 4 substituents selected from the group consisting of: hydrogen, halogen, nitro, cyano, $C_1$-$C_4$ alkoxy, $C_1$-$C_4$ thioalkyl, $C_1$-$C_4$ perfluoroalkyl, $C_1$-$C_4$ perfluoroalkoxy, $C_1$-$C_4$ acyl, $C_1$-$C_4$ amido, $C_1$-$C_4$ alkoxycarbonyl and phenyl, and particularly preferably phenyl; and R and R' each independently denote (1) an aryl group having 6 to 17 carbon atoms and preferably phenyl, or pyridinyl, optionally substituted with one or more of an alicyclic carboxyl group, an alicyclic heterocyclic carboxyl group, an aliphatic carboxyl group or an aromatic carboxyl group; (2) a saturated hydrocarbyl group having 1 to 18 carbon atoms ($C_nH_{2n+1}$, where n=an integer from 1 to 18), preferably a linear alkyl or alkoxy group having 2 to 17 carbon atoms and optionally substituted with one or more of an alicyclic carboxyl group, an alicyclic heterocyclic carboxyl group, an aliphatic carboxyl group or an aromatic carboxyl group; or (3) a 4- to 6-membered heterocyclic group containing 1 to 3 nitrogen, sulfur, or oxygen atoms and optionally substituted with 1 to 4 substituents selected from the group consisting of: hydrogen, halogen, nitro, cyano, $C_1$-$C_4$ alkoxy, $C_1$-$C_4$ thioalkyl, $C_1$-$C_4$ perfluoroalkyl, $C_1$-$C_4$ perfluoroalkoxy, $C_1$-$C_4$ acyl, $C_1$-$C_4$ amido, $C_1$-$C_4$ alkoxycarbonyl, phenyl, an alicyclic carboxyl group, an alicyclic heterocyclic carboxyl group, an aliphatic carboxyl group, and an aromatic carboxyl group.

Without being bound by theory, it is found in the present invention that when an aromatic carbamate is used to replace the isocyanate in the preparation of an amide or polyamide, the occurrence of side reactions can be effectively inhibited, and thus the amide or polyamide product can be obtained with a purity of 85% or higher, preferably 90% or higher, particularly preferably 95% or higher, and most preferably 98% or higher, and a yield of 85% or higher, preferably 90% or higher, particularly preferably 95% or higher, and most preferably 98% or higher. In addition to the advantages of high purity, high yield, and high performance mentioned above, replacing the isocyanate with an aromatic carbamate also leads to the advantages of simple process, easy storage, reduced toxicity and environmental protection.

According to an embodiment of the present invention, if an N-aryl carbamate, preferably an N-aryl carbamate of formula [Ar—NHCOO—Ar] or an alkyl N-aryl carbamate of formula [Ar—NHCOO—R″], where Ar has the same meaning as defined above, R″ is a saturated hydrocarbyl group having 1 to 18 carbon atoms ($C_nH_{2n+1}$, where n=an integer from 1 to 18), and preferably a linear alkyl having 2 to 17 carbon atoms, is used in place of the isocyanate in the catalyzed thermal reaction, the problem of low yield resulting from the reaction of the highly reactive isocyanate with water or self-trimerization thereof to produce urea and other by-products can be avoided.

Specifically, a method of the present invention for preparing an amide through a route using a non-isocyanate raw material comprises:

(a) thermally cracking an aromatic carbamate in a polymerization solvent, to form an aromatic isocyanate solution;

(b) subjecting the aromatic isocyanate to a self-condensation reaction in the presence of a CDI catalyst, preferably a cyclic phosphorus-based compound, to form an aromatic carbodiimide;
(c) prompting the reaction between the aromatic carbodiimide and a carboxylic acid, to form a reaction intermediate aromatic N-acyl urea; and
(d) thermally cracking the aromatic N-acyl urea, to form the aromatic isocyanate and the amide product.

The aromatic carbamate comprises a single aromatic carbamate group, and/or the carboxylic acid comprises a single carboxyl functional group. The catalyzed thermal reaction of Steps (b) to (d) is performed repeatedly, and preferably the main reaction route of the catalyzed thermal reaction of Steps (b) to (d) is a sequential self-repetitive reaction (SSRR) route.

According to an embodiment of the present invention, the method of the present invention for preparing an amide through a catalyzed thermal reaction route using a non-isocyanate raw material cannot be completed instantaneously in one step, but is carried out gradually and repeatedly in one pot of the instantly formed aromatic isocyanate solution in the polymerization solvent in the presence of the catalyst, until the starting material aromatic carbamate is completely consumed. The whole reaction process may be observed and traced by Fourier transform infrared spectroscopy (FTIR).

In the method of the present invention for preparing an amide through a catalyzed thermal reaction route using a non-isocyanate raw material as described above, when the carboxylic acid used comprises a single carboxyl functional group, the prepared product comprises an amide.

A method of the present invention for preparing a polyamide with an aromatic carbamate through a catalyzed thermal reaction route using a non-isocyanate starting material comprises
(a) thermally cracking an aromatic carbamate (N,N'-aromatic biscarbamate) in a polymerization solvent, to form an aromatic diisocyanate solution;
(b) subjecting the newly produced aromatic isocyanate to a self-condensation reaction in the presence of a CDI catalyst, to form an aromatic carbodiimide;
(c) reacting the aromatic carbodiimide with a carboxylic acid, to form a reaction intermediate aromatic N-acyl urea; and
(d) thermally cracking the aromatic N-acyl urea, to form ½ of the mole number of the aromatic isocyanate for reaction and ½ of the mole number of the polyamide product.

The catalyzed thermal reaction of Steps (b) to (d) is performed repeatedly, and preferably the main reaction route of the catalyzed thermal reaction of Steps (b) to (d) is a sequential self-repetitive reaction (SSRR) route.

In the method of the present invention for preparing an amide or polyamide with an aromatic carbamate through a catalyzed thermal reaction route using a non-isocyanate starting material as described above, when the aromatic carbamate used comprises at least two aromatic carbamate groups, and the carboxylic acid used comprises at least two carboxyl functional groups, the prepared product comprises a polyamide.

Carboxylic Acid

In the method of the present invention for preparing an amide or polyamide with an aromatic carbamate through a catalyzed thermal reaction route using a non-isocyanate starting material as described above, the species of the carboxylic acid used is not particularly limited, and an aliphatic or aromatic carboxylic acid optionally having an electron withdrawing or donating group may be used in the practice of the present invention. A suitable carboxylic acid is selected from the group consisting of a monocarboxylic acid, such as acetic acid or benzoic acid, a dicarboxylic acid, such as adipic acid or azelaic acid, and a mixture thereof. The dicarboxylic acid is selected from the group consisting of an aliphatic diacid, preferably a long-chain aliphatic diacid having 2 to 18 carbon atoms, an aromatic diacid, such as terephthalic acid, isophthalic acid, or 4,4'-(hexafluoroisopropylidene)-bis(benzoic acid) (HFI-BBA), an aryl aliphatic diacid, such as fluoro-aliphatic aryl diacid, and a mixture thereof. The carboxylic acid is particularly preferably selected from the group consisting of acetic acid, benzoic acid, oxalic acid, succinic acid, adipic acid, azelaic acid, terephthalic acid, isophthalic acid and a mixture thereof.

CDI Catalyst

CDI catalysts are widely described in the literature, and well known to those skilled in the art. Suitable CDI catalysts include, but are not limited to, a phosphorus-based compound, a cyclic phosphorus-based compound or a derivative thereof. Examples of the CDI catalysts include 3-methyl-3-phospolene oxide (MPO), 1,3-dimethyl-3-phospolene oxide (DMPO), 3-methyl-phenyl-3-phosphorene-1-oxide (MPPO), 1,3-dimethyl-1,3,2-diazaphophorolidine, triphenylarsenic oxide, and the CDI catalysts described in Tetrahedron Report R101 in Tetrahedron (Vol. 37, pages 233-284, 1981), page 235; and Angew. Chem. internt. Edit. Vol. 1, 621 (1962). Preferably, MPPO readily available from the chemical raw materials market is used as the CDI catalyst in the present invention. The content of the literature is incorporated herein by reference.

Polymerization Solvent

As is well known to those of ordinary skill in the art, the aromatic carbodiimide implicated in the method for preparing an amide or polyamide through a catalyzed thermal reaction route using a non-isocyanate starting material is obtained by converting, in the presence of a CDI catalyst, the aromatic isocyanate formed through thermal cracking of the aromatic carbamate. Any suitable polymerization solvent may be used in the reaction, provided that no active hydrogen is contained in the structure of the solvent. Examples include, but are not limited to, toluene, chlorobenzene, anhydrous tetrahydrofuran (THF), diphenyl ether (DPE), tetramethylene sulfone (TMS), γ-butyrolactone (GBL), and an ester solvent. The species of the solvent suitable for use in the reaction can be easily determined by those skilled in the art. Preferably, all of the starting material is dissolved in a suitable solvent, such as anhydrous tetrahydrofuran (THF), diphenyl ether (DPE), tetramethylene sulfone (TMS), γ-butyrolactone (GBL), and an ester solvent, to carry out the catalyzed thermal reaction process and produce an intended amide or polyamide. The species of the solvent suitable for use in the reaction can be easily determined by those of ordinary skill in the art.

In the method of the present invention for preparing an amide or polyamide through a catalyzed thermal reaction route using a non-isocyanate raw material as described above, the polymerization solvent comprises a polymerization solvent containing no nitrogen in its molecular structure, i.e., a nitrogen-free polymerization solvent, and preferably the polymerization solvent consists essentially of a nitrogen-free polymerization solvent. Preferably, the water in the polymerization solvent comprising the nitrogen-free polymerization solvent is present in an amount of <100 ppm or less, and preferably <50 ppm or less.

In the method of the present invention for preparing an amide or polyamide through a catalyzed thermal reaction route using a non-isocyanate raw material as described above, the nitrogen-free polymerization solvent includes tetramethylene sulfone (TMS) and/or γ-butyrolactone (GBL).

According to an embodiment of the method of the present invention for preparing an amide or polyamide through a catalyzed thermal reaction route, a nitrogen-free polymerization solvent, such as tetramethylene sulfone (TMS) and/or γ-butyrolactone (GBL), is used as a polymerization solvent in the synthesis of a polyamide. When analyzing the molecular weight distribution of the polyamide by Gel Permeation Chromatography (GPC (NMP column)), the inventors of the present invention have unexpectedly found that the polyamide prepared by using the method of the present invention has a more concentrated molecular weight distribution, compared with a polyamide prepared by using a nitrogen containing polymerization solvent, such as anhydrous N-methyl-2-pyrrolidone (NMP). The GPC results show that the molecular weight distribution with a short retention time is reduced to 1% or less in comparison with 20 to 48% obtained from the use of anhydrous N-methyl-2-pyrrolidone as a polymerization solvent. Moreover, the $^1$H NMR results also show that unlike the polyamides synthesized by using anhydrous N-methyl-2-pyrrolidone as a polymerization solvent, the shift of the N—H peak due to the use of γ-butyrolactone and/or tetramethylene sulfone as a polymerization solvent to synthesis polyamides cannot be observed in the $^1$H NMR spectrum. Without being bound by theory, it is believed that a linear polyamide of high purity and narrow molecular weight distribution can be produced by using a nitrogen-free polymerization solvent, the thermal properties of which tend to be further improved compared with the prior art. According to an embodiment of the present invention, the Tg of polyamides synthesized with MDI and 4,4'-(hexafluoroisopropylidene)-bis(benzoic acid) (HFI-BBA) in anhydrous N-methyl-2-pyrrolidone as a polymerization solvent in the prior art is only 246° C., while the Tg of polyamides synthesized with 4,4'-(hexafluoroisopropylidene)-bis(benzoic acid) (HFI-BBA) and MDI in γ-butyrolactone as a polymerization solvent in the present invention can be increased to 272° C. It is believed that the thermal properties are improved because high-purity linear polyamides are synthesized by using γ-butyrolactone, i.e., a nitrogen-free polymerization solvent, as the polymerization solvent.

It is believed that the anhydrous N-methyl-2-pyrrolidone used in the prior art is a nitrogen-containing polymerization solvent and is amenable to side reaction with the isocyanate involved in the catalyzed thermal reaction process, to produce a non-linear by-product having a cyclic and branched structure. The inventors of the present invention have found that in a nitrogen-containing polymerization solvent system (e.g., a polymerization solvent comprising anhydrous N-methyl-2-pyrrolidone), the polyamides prepared with the isocyanate disclosed in the prior art or with the aromatic carbamate disclosed in the present invention both have a bimodal molecular weight distribution (as determined by GPC). This results show that that the purity and thermal properties of the main product would be influenced by the nitrogen-containing polymerization solvent. As described above, the thermal properties of the polyamide prepared by using a nitrogen-containing polymerization solvent are not as good as those of the polyamide prepared by using a nitrogen-free polymerization solvent (e.g., tetramethylene sulfone or γ-butyrolactone polymerization solvent) in the present invention. Therefore, when an amide or polyamide is prepared by a catalyzed thermal reaction, the polymerization solvent used should not be a nitrogen-containing polymerization solvent, so that the product yield is increased and the production of by-products is inhibited. Moreover, when used as a starting material in the reaction, the aromatic carbamate disclosed in the present invention is advantageous over the isocyanate disclosed in the prior art.

Reaction Temperature

In the method of the present invention for preparing an amide or polyamide through a catalyzed thermal reaction route using a non-isocyanate raw material as described above, the thermal cracking in Step (a) takes place at a temperature of 120° C. or higher, preferably 160° C. or higher, and particularly preferably 180° C. or higher.

According to an embodiment of the present invention, the reaction may be carried out at a temperature of 120° C. or at a temperature in the range of 120° C. to 300° C., preferably 160° C. to 280° C., more preferably 180° C. to 260° C., and particularly preferably 200° C. to 240° C. in a single reactor via a one-pot method, where preferably, the materials may be optionally fed in multiple manners.

According to another embodiment of the present invention, in the catalyzed thermal reaction route exemplified by the preparation of an amide as described above, when R and R' are phenyl, the decomposition temperature at which production of transient isocyanate and a phenol is facilitated is about 120 to 220° C.; and when R and R' are alkyl groups, the decomposition temperature of the carbamate is elevated to 180 to 260° C.

Aromatic Carbamate and Preparation Method Thereof

In the method of the present invention for preparing an amide or polyamide through a catalyzed thermal reaction route using a non-isocyanate raw material as described above, the aromatic carbamate is at least one selected from the group consisting of phenyl N-phenylcarbamate (PPC), 4,4'-methylene-diphenylene bis-phenylcarbamates (4,4'-DP-MDC), 4,4'-oxy diphenylene bis-phenylcarbamates (4,4'-DP-ODC), and 1,4-phenylene bis-phenylcarbamate (1,4'-PPDC).

According to non-limiting embodiments as shown in Table 1 below, the inventors of the present invention have unexpectedly found that for various carboxylic acids tested, when the amide is synthesized through a reaction scheme where the isocyanate or the aromatic carbamate is individually used as the reaction starting material and reacted with an organic carboxylic acid for synthesizing an amide monomer, both the purity and the yield of the amide obtained when the isocyanate is used as the reaction starting material are lower than those obtained when the aromatic carbamate is used, as shown in Table 1.

TABLE 1

Comparison of yield and melting point range of amide products prepared
by using various isocyanates or aromatic carbamates

| No. | Isocyanate or aromatic carbamate | Carboxylic acid |
|---|---|---|
| a | PhNCO | benzoic acid |
| b | PhNCO | |
| c | PhNHC(O)OPh | |
| d | PhNCO | 4,4'-(hexafluoroisopropylidene)dibenzoic acid |
| e | PhNHC(O)OPh | |
| f | PhNCO | HOOC-(CH$_2$)$_7$-COOH |
| g | PhNHC(O)OPh | |
| h | O=C=N-C$_6$H$_4$-(CH$_2$)$_3$-C$_6$H$_4$-N=C=O | benzoic acid |
| i | PhO-C(O)NH-C$_6$H$_4$-CH$_2$-C$_6$H$_4$-NH-C(O)-OPh | |

TABLE 1-continued

Comparison of yield and melting point range of amide products prepared by using various isocyanates or aromatic carbamates

| No. | Amide product | Yield (%) | Melting point range (° C.) |
|---|---|---|---|
| a | | 73 | (157.2-168.0)[j] |
| b | | 78 | 163.7-167.2 |
| c | | 98 | 163.2-165.0 |
| d | | 77 | 294.5-297.7 |
| e | | 97 | 295.0-297.5 |
| f | | 84 | 183.1-188.7 |
| g | | 90 | 184.0-186.3 |
| h | | 91 | 253.5-257.3 |
| i | | 91 | 253.8-257.0 |

[j]synthesised in NMP, 2.9% diphenyl urea.
$R_1$ has the same meaning as defined for R' above.

As described above, the yield of the amide prepared when the aromatic carbamate, such as N-phenyl aromatic carbamate, is reacted with an organic carboxylic acid is increased. The reason may be that the aromatic isocyanate used in the prior art is highly reactive and prone to trimerization side reaction in an alkaline solution containing nitrogen, and may also be reacted with water in the solution to produce a urea by-product. Due to the high melting point and stability, the urea is difficult to further decompose and convert into the isocyanate for reuse, resulting in a reduced yield of the amide product.

Method for Preparing Aromatic Carbamate Precursor

Another object of the present invention is to provide a novel method for preparing an aromatic carbamate, which comprises: reacting an aromatic amine with diphenyl carbonate (DPC) in the presence of a carbonylation catalyst, to produce an aromatic carbamate, where the carbonylation catalyst comprising a complex formed by a carboxylic acid and a poly(tertiary amine)-type alkaline compound. The reaction formula is shown below:

where $Ar_3$ and $Ar_4$ are each independently an aryl group having 6 to 17 carbon atoms and preferably phenyl, or pyridinyl, or a 4- to 6-membered heterocyclic group containing 1 to 3 nitrogen, sulfur, or oxygen atoms and substituted with 1 to 4 substituents selected from the group consisting of hydrogen, halogen, nitro, cyano, $C_1$-$C_4$ alkoxy, $C_1$-$C_4$ thioalkyl, $C_1$-$C_4$ perfluoroalkyl, $C_1$-$C_4$ perfluoroalkoxy, $C_1$-$C_4$ acyl, $C_1$-$C_4$ amido, $C_1$-$C_4$ alkoxycarbonyl and phenyl, and particularly preferably phenyl.

According to a preferred embodiment of the present invention, in the method for preparing an aromatic carbamate of the present invention, the aromatic amine includes aniline, 4,4'-methylenedianiline (4,4'-MDA), 4,4'-oxydianiline (ODA), p-phenylenediamine (PPDA) or 1,5-diaminonaphthalene (NDA).

According to an embodiment of the present invention, the combination of the carboxylic acid and the poly(tertiary amine)-type alkaline compound involved in the carbonylation catalyst is preferably a compound that is a liquid at room temperature, and more preferably both of the carboxylic acid and the poly(tertiary amine)-type alkaline compound are liquid at room temperature. Besides the advantage of convenience in delivery and addition to the reactor, the conversion reaction can be carried out at room temperature, to provide a high efficiency and high selectivity. Thus, an intended aromatic carbamate can be prepared.

According to an embodiment of the present invention, the carboxylic acid in the carbonylation catalyst is selected from the group consisting of the compounds represented by the formula below:

$R^6$—COOH in which $R^6$ denotes alkyl, cycloalkyl, aryl, heterocycyl or a combination thereof. Preferably $R^6$ is selected from the group consisting of:
  (1) an alkyl group having 2 to 17 carbon atoms, such as ethyl, butyl, and t-butyl;
  (2) a cycloalkyl group having 5 to 16 carbon atoms, such as cyclopentyl, and cyclohexyl;
  (3) an aryl group having 7 to 17 carbon atoms, such as phenyl and naphthyl; and
  (4) a heterocyclic group having 5 to 16 carbon atoms, such as furanyl, thienyl and pyridyl.

The carboxylic acid is preferably selected from p-t-butyl benzoic acid, p-anisic acid, isobutyric acid, propanoic acid, butyric acid, acetic acid and pivalic acid.

The poly(tertiary amine)-type alkaline compound in the carbonylation catalyst is selected from the group consisting of a triazine compound, such as 1,3,5-tris(3-dimethylamino)propyl)hexahydro-s-triazine ([Polycat 41]) (containing six tertiary-amine groups), bis(N,N'-dimethylaminoethyl)ether ([NIAX A-99 and BL-19]) or N,N'-dimethylaminoethyl-N-methylethanolamine ([DABCO T]) (containing two tertiary-amine groups), or tris(dimethylaminomethyl)phenol ([TMR 30; DMP-30]) or N,N'-dimethylaminoethyl morpholine ([DABCO XDM]) (containing three tertiary-amine groups); or other commercially available polyurethane (PU) catalyst product, for example: Niax TMBDA or and the tertiary-amine catalyst products supplied by Air Products and Chemicals, Inc., such as Polycat 5, Polycat 6 or Polycat 9.

According to a preferred embodiment of the present invention, in the method for preparing an aromatic carbamate of the present invention, the weight ratio of the carboxylic acid to the poly(tertiary amine)-type alkaline compound is from 6:1 to 10:1, preferably from 7:1 to 9:1, and particularly preferably 8:1 in the carbonylation catalyst comprising a complex formed by the carboxylic acid and the poly (tertiary amine)-type alkaline compound.

According to a non-limiting embodiment of the method for preparing an aromatic carbamate according to the present invention, the prepared aromatic carbamate comprises phenyl N-phenylcarbamate (PPC).

According to a non-limiting embodiment of the method for preparing an aromatic carbamate according to the present invention, the prepared aromatic carbamate comprises 4,4'-methylene-diphenylene bis-phenylcarbamates (4,4'-DP-MDC).

According to a non-limiting embodiment of the method for preparing an aromatic carbamate according to the present invention, the prepared aromatic carbamate comprises 4,4'-oxy diphenylene bis-phenylcarbamates (4,4'-DP-ODC).

According to a non-limiting embodiment of the method for preparing an aromatic carbamate according to the present invention, the prepared aromatic carbamate comprises 1,4-phenylene bis-phenylcarbamate (1,4'-PPDC).

It is unexpectedly found that in the method for preparing an aromatic carbamate of the present invention, the yield of the aromatic carbamate obtained by reacting an aromatic amine, preferably aniline, 4,4'-methylenedianiline, 4,4'-oxydianiline or p-phenylenediamine, with diphenyl carbonate under the catalysis of isobutyric acid and the triazine compound, preferably 1,3,5-tris(3-(dimethylamino)propyl) hexahydro-1,3,5-triazine is 80% or higher, preferably 90% or higher, and particularly preferably 95% or higher. By comparing the $^1$H-NMR spectra and melting points of the products synthesized in the present invention with those synthesized in the prior art, the integration intensity and position of the hydrogen peak in the NMR spectra, the melting point, and other characteristics of the aromatic carbamate shows good agreements between them.

BRIEF DESCRIPTION OF THE DRAWING

The invention will be described according to the appended drawings in which.

DETAILED DESCRIPTION OF THE INVENTION

All numerical values expressing the contents, proportions, and physical characteristics, etc. used in the specification and claims are to be construed as being modified by the term "about." Accordingly, unless otherwise indicated, the numerical values set forth in the following description and the appended claims may vary depending on the intended and/or desired characteristics of the present invention. At least, and without attempt to limit the application of the equivalence principle to the scope of the claims, the numerical parameters should be interpreted in accordance with the number of significant digits disclosed and by the application of general rounding.

All ranges disclosed herein are to be construed as covering any and all sub-ranges and values encompassed therein.

For example, the range of "1 to 10" should be considered to include any and all sub-ranges and values between a minimum value of 1 and a maximum value of 10, inclusive, that is, all the sub-ranges and values starting with a minimum value of 1 or greater and ending with a maximum value of 10 or lower, for example, from 1 to 6.7, from 3.2 to 8.1 or from 5.5 to 10, and 2.5, 4.3, 7.1 or 9.

Before discussing a number of non-limiting embodiments of the present invention, it is to be understood that the present invention is not limited in its application to the details of the specific and non-limiting embodiments shown and described herein, because the present invention may have other embodiments. For example, the 4,4'-(hexafluoroisopropylidene)-bis (benzoic acid) used in the present embodiment is a highly soluble compound, which is exemplified as a diacid raw material in an example of the present invention, and the resulting polyamide derived therefrom also has high solubility. Therefore, the analysis of the molecular weight of the product by GPC is facilitated, and the product can be easily fabricated into a sample (such as a film) for testing the physical properties, whereby the product can be effectively compared with those products prepared through other processes. In addition, the terminology used herein to discuss the present invention is provided for the purpose of illustration, instead of limitation. Unless otherwise specified, the following discussion of similar numbers refers to similar elements. It will be understood by those skilled in the art that the present invention can be utilized to the utmost extent in accordance with the above disclosure and the following Examples. The following examples are merely illustrative of the manner that the skilled artisan may implement the present application, and not intended to limit the rest of the disclosure in any way.

Example 1-1: Preparation of phenyl n-phenylcarbamate from aniline and diphenyl carbonate 1,3,5-tris(3-(dimethylamino)propyl)hexahydro-1,3,5-triazine (0.01 g) and isobutyric acid (0.08 g) were used as co-catalysts and added to a three-neck flask, and toluene (150 ml), aniline (9.3 g, 0.1 mole), and diphenyl carbonate (64.2 g, 0.3 mole) were also added. The mixed solution was mechanically stirred at 55° C. for 48 hours and then cooled to −10° C., to obtain a precipitate. The precipitate was separated by filtration, washed with toluene, and dried under vacuum to obtain 21.0 g of phenyl N-phenylcarbamate with an yield of about 98%.

Figure 1:
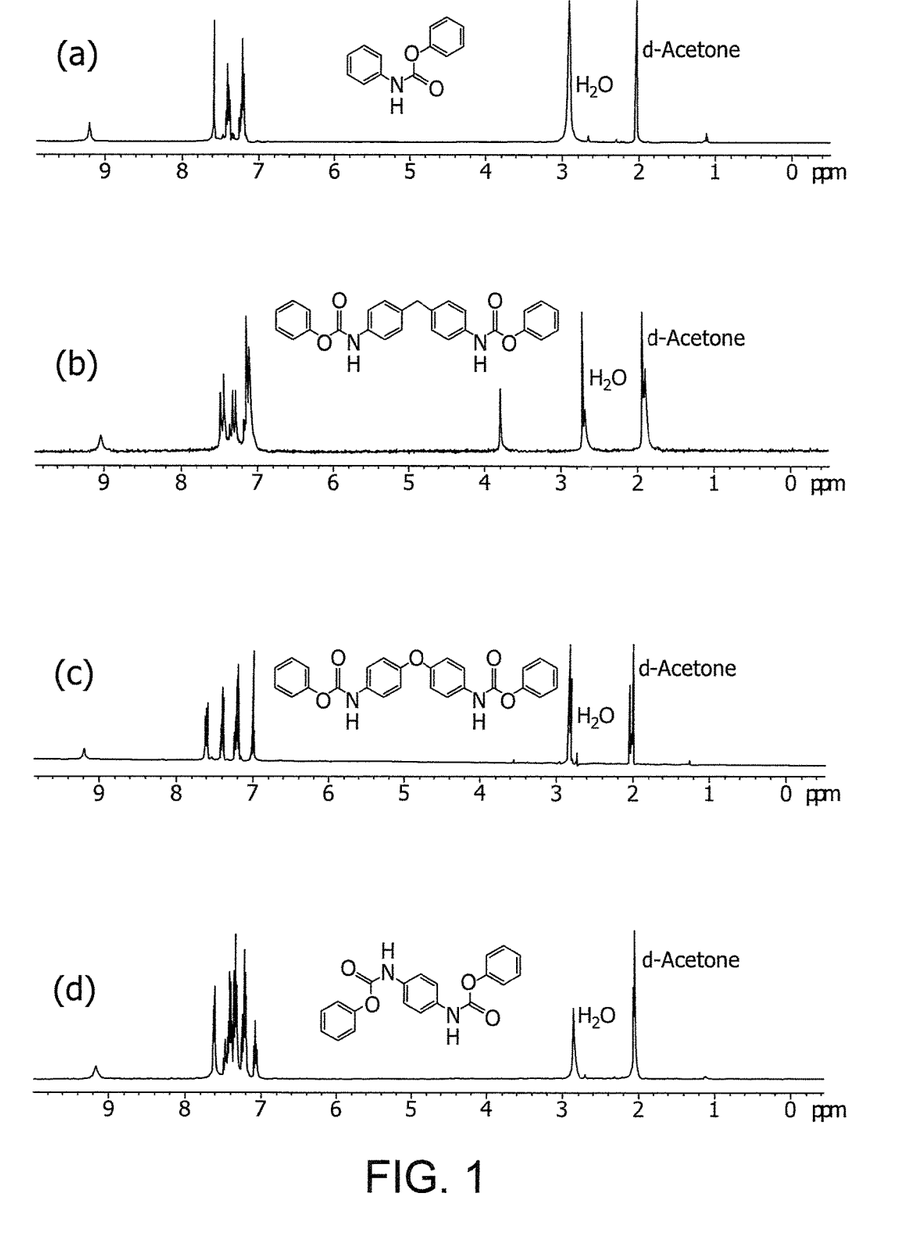
FIG. 1 shows the $^1$H-NMR spectra of aromatic carbamates synthesized with various aromatic amines.

The FT-IR (KBr) spectrum shows a peak of ν (C=O) at 1714 cm$^{-1}$, and a peak of ν (N—H) at 3319 cm$^{-1}$. The $^1$H NMR (400 MHz, Acetone-d$_6$) spectrum shows that δ (Ar—H) is at 7.09 to 7.7 and δ (s, $^1$H, N—H) is at 9.2. The prepared phenyl N-phenylcarbamate has a melting point ranging from 134.1 to 135.3° C., as determined by differential scanning calorimetry (DSC; lit 135° C.). The analysis results of the separated product phenyl N-phenylcarbamate prepared by the method according to the present invention are the same as those of the sample shown in Cas. Number: 4930-03-4. The integration intensity and position of the hydrogen peak obtained by analyzing the $^1$H-NMR spectrum and the melting point of the target product are in agreement with those described in the literature (FIG. 1).

Example 1-2: Preparation of 4,4'-methylene-diphenylene bis-phenylcarbamate from 4,4'-methylenedianiline and diphenyl carbonate 1,3,5-tris(3-(dimethylamino)propyl)hexahydro-1,3,5-triazine (0.01 g) and isobutyric acid (0.08 g) were used as co-catalysts and added to a 500 ml three-neck flask, and toluene (150 ml), 4,4'-methylenedianiline (19.8 g, 0.1 mole) and diphenyl carbonate (128.5 g, 0.6 mole) were also added. The mixed solution was mechanically stirred at 55° C. for 48 hours under a non-nitrogen atmosphere, and then cooled to room temperature, to obtain a precipitate. The precipitate was separated by filtration, and dried to obtain 42.3 g of 4,4'-methylene-diphenylene bis-phenylcarbamate with a yield of about 96.4%).

The FT-IR (KBr) spectrum shows a peak of ν (C=O) at 1723 cm, and a peak of ν (N—H) at 3335 cm$^{-1}$. The $^1$H NMR (400 MHz, Acetone-d$_6$) spectrum shows that δ(Ar—H) is at 6.9 to 7.7, and δ (s, $^1$H, N—H) is at 9.2. The prepared 4,4'-methylene-diphenylene bis-phenylcarbamate has a melting point ranging from 195.0 to 197.2° C., as determined by DSC. The analysis results of the separated product 4,4'-methylene-diphenylene bis-phenylcarbamate prepared by the method according to the present invention are the same as those of the sample shown in Chen H. Y., Pan W. C., Lin C. H., Huang C. Y. and Dai S. A., Journal of Polymer Research, 19(2), 9754-9765, 2012. The integration intensity and position of the hydrogen peak obtained by analyzing the $^1$H-NMR spectrum and the melting point of the target product are in agreement with those described in the literature (FIG. 1).

Example 1-3: Preparation of 4,4'-oxy diphenylene bis-phenylcarbamate from 4,4'-oxydianiline and diphenyl carbonate 1,3,5-tris(3-(dimethylamino)propyl)hexahydro-1,3,5-triazine (0.01 g) and isobutyric acid (0.08 g) were used as co-catalysts and added to a 500 ml three-neck flask, and toluene (150 ml), 4,4'-oxydianiline (20 g, 0.1 mole), and diphenyl carbonate (128.5 g, 0.6 mole) were also added. The mixed solution was mechanically stirred at 55° C. for 48 hours under a non-nitrogen atmosphere, and then cooled to room temperature, to obtain a precipitate. The precipitate was separated by filtration, and dried to obtain 42.7 g of 4,4'-oxy diphenylene bis-phenylcarbamates with a yield of about 97%.

The FT-IR (KBr) spectrum shows a peak of ν (C=O) at 1722 cm$^{-1}$, and a peak of ν (N—H) at 3340 cm$^{-1}$. The $^1$H NMR (400 MHz, Acetone-d6) spectrum shows that δ (Ar—H) is at 6.9 to 7.7, and δ (s, $^1$H, N—H) is at 9.2. The prepared 4,4'-oxy diphenylene bis-phenylcarbamate has a melting point ranging from 205.2 to 207.0° C., as determined by DSC. The analysis results of the separated product 4,4'-oxy diphenylene bis-phenylcarbamate prepared by the method according to the present invention are the same as those of the sample shown in U.S. Pat. No. 3,620,664. The integration intensity and position of the hydrogen peak obtained by analyzing the $^1$H-NMR spectrum and the melting point of the target product are in agreement with those described in the literature (FIG. 1).

Example 1-4: Preparation of 1,4-phenylene bis-phenylcarbamate from p-phenylenediamine and diphenyl carbonate 1,3,5-tris(3-(dimethylamino)propyl)hexahydro-1,3,5-triazine (0.01 g) and isobutyric acid (0.08 g) were used as co-catalysts and added to a 500 ml three-neck flask, and toluene (150 ml), p-phenylenediamine (10.08 g, 0.1 mole), and diphenyl carbonate (128.5 g, 0.6 mole) were also added. The mixed solution was mechanically stirred at 55° C. for 48 hours under a non-nitrogen atmosphere, and then cooled to room temperature (about 25° C.), to obtain a precipitate. The precipitate was separated by filtration, and dried to obtain 34 g of 1,4-phenylene bis-phenylcarbamate with a yield of about 98%.

The FT-IR (KBr) spectrum shows a peak of ν (C=O) at 1722 cm$^{-1}$, and a peak of ν (N—H) at 3340 cm$^{-1}$. The $^1$H NMR (400 MHz, Acetone-d) spectrum shows that δ(Ar—H) is at 72 to 7.6, and δ(s, $^1$H, N—H) is at 9.2. The prepared 1,4-phenylene bis-phenylcarbamate has a melting point ranging from 237.1 to 238.7° C., as determined by DSC. The analysis results of the separated product 1,4-phenylene bis-phenylcarbamate prepared by the method according to the present invention are the same as those of the sample shown in Cas. Number: 22824-04-0. The integration intensity and position of the hydrogen peak obtained by analyzing the $^1$H-NMR spectrum and the melting point of the target product are in agreement with those described in the literature (FIG. 1).

The yields and melting points of the aromatic carbamates prepared with various aromatic amines and diphenyl carbonate in the presence of isobutyric acid and 1,3,5-tris(3-(dimethylamino)propyl)hexahydro-1,3,5-triazine as catalysts in Example 1 are listed in Table 2 below.

were also added. The mixed solution was mechanically stirred at 200° C. for 1 hour under a nitrogen atmosphere, and then cooled to room temperature, to obtain a precipitate. The precipitate was washed with water (1500 ml), filtered and dried to obtain 6.0 g of PA[MDI/HFI-BBA]$_{GBL}$ polyamide in a form of white fibers with a yield of about 97%).

Figure 2:
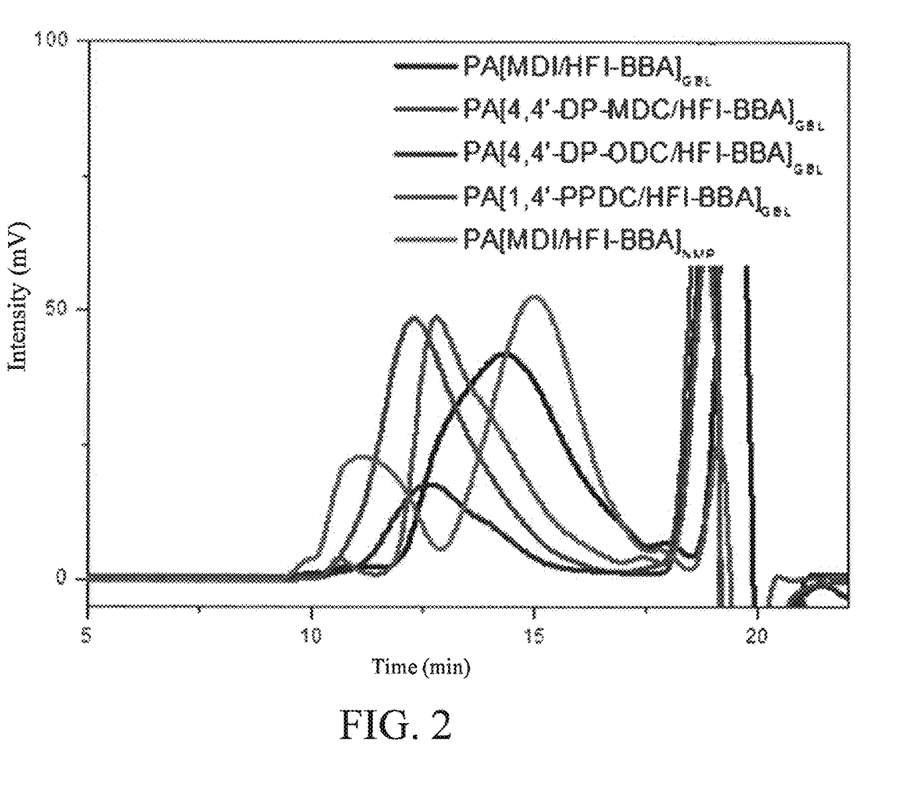
FIG. 2 shows the Gel Permeation Chromatography (GPC) analysis results of polyamides synthesized with an aromatic carbamate or a polyisocyanate in NMP/GBL as a polymerization solvent.

The gel permeation chromatography analysis result (as shown in FIG. 2) shows that the prepared PA[MDI/HFI-BBA]$_{GBL}$ polyamide has a number average molecular weight (Mn) and a weight average molecular weight (Mw) of 4,400 g/mol and 11,200 g/mol, respectively. The DSC analysis result shows that Td (5%) is 432° C. and the glass transition temperature Tg is 272° C. under nitrogen atmosphere.

Example 2-2: Synthesis of PA[4,4'-DP-MDC/HFI-BBA]$_{GBL}$ polyamide with 4,4'-methylene-diphenylene bis-phenylcarbamate and 4,4'-(hexafluoroisopropylidene)-bis(benzoic acid) Through Non-Isocyanate Route MPPO (0.05 g) as a CDI catalyst was added to a three-neck flask, and γ-butyrolactone (150 ml), 4,4'-methylene-

TABLE 2

Yields and melting points of aromatic carbamates prepared with various aromatic amines and diphenyl carbonate

| No. | Aromatic amine | Aromatic carbamate | Name | Yield (%) | Melting point (° C.) |
|---|---|---|---|---|---|
| 1-1 | aniline | phenyl phenylcarbamate | PPC | 98% | 134.1-135.3 |
| 1-2 | 4,4'-methylenedianiline | 4,4'-methylenediphenylene bis-phenylcarbamate | 4,4'-DP-MDC | 96% | 195.0-197.2 |
| 1-3 | 4,4'-oxydianiline | 4,4'-oxydiphenylene bis-phenylcarbamate | 4,4'-DP-ODC | 97% | 205.2-207.0 |
| 1-4 | 1,4-phenylenediamine | 1,4-phenylene bis-phenylcarbamate | 1,4-PPDC | 98% | 237.1-238.7 |

Comparative Example 2-1: Synthesis of PA[MDI/HFI-BBA]$_{GBL}$ polyamide with methylene diphenyl diisocyanate (MDI) and 4,4'-(hexafluoroisopropylidene)-bis(benzoic acid) (HFI-BBA)

MPPO (0.05 g) as a CDI catalyst was added to a 500 ml three-neck flask, and γ-butyrolactone (150 ml), methylene diphenyl diisocyanate (2.5 g, 0.01 mole), and 4,4'-(hexafluoroisopropylidene)-bis(benzoic acid) (3.92 g, 0.01 mole) were also added. The mixed solution was mechanically stirred at 200° C. for 1 hour under a nitrogen atmosphere, and then cooled to room temperature, to obtain a precipitate. The precipitate was washed with water (1500 ml), filtered and dried to obtain 6.1 g of PA[4,4'-DP-MDC/HFI-BBA]$_{GBL}$ polyamide in a form of white fibers with a yield of about 98%.

diphenylene bis-phenylcarbamates (3.84 g, 0.01 mole), and 4,4'-(hexafluoroisopropylidene)-bis(benzoic acid) (3.92 g, 0.01 mole) were also added.

The gel permeation chromatography analysis result (as shown in FIG. 2) shows that the prepared PA[4,4'-DP-MDC/HFI-BBA]$_{GBL}$ polyamide has a number average molecular weight (Mn) and a weight average molecular weight (Mw) of 17,000 g/mol and 66,000 g/mol, respectively. The DSC analysis result shows that Td (5%) is 466° C. and the glass transition temperature Tg is 272° C. under nitrogen atmosphere.

Example 2-3: Synthesis of PA[4,4'-DP-ODC/HFI-BBA]$_{GBL}$ polyamide with 4,4'-oxy diphenylene bis-phenylcarbamates and 4,4'-(hexafluoroisopropylidene)-bis(benzoic acid) Through Non-Isocyanate Route MPPO (0.05 g) as a CDI catalyst was added to a 250 ml three-neck flask, and γ-butyrolactone (150 ml), 4,4'-oxy diphenylene bis-phenylcarbamates (4.4 g, 0.01 mole), and 4,4'-(hexafluoroisopropylidene)-bis(benzoic acid) (3.92 g, 0.01 mole) were also added. The mixed solution was mechanically stirred at 200° C. for 1 hour under a nitrogen atmosphere, and then cooled to room temperature, to obtain a precipitate. The precipitate was washed with water (1500 ml), filtered and dried to obtain 5.73 g of PA[4,4'-DP-ODC/HFI-BBA]$_{GBL}$ polyamide in a form of white fibers with a yield of about 96%.

The gel permeation chromatography analysis result (as shown in FIG. 2) shows that the prepared PA[4,4'-DP-ODC/HFI-BBA]$_{GBL}$ polyamide has a number average molecular weight (Mn) and a weight average molecular weight (Mw) of 15,000 g/mol and 40,400 g/mol, respectively. The DSC analysis result shows that Td (5%) is 440° C. and the glass transition temperature Tg is 270° C. under nitrogen atmosphere.

Example 2-4: Synthesis of PA[1,4'-PPDC/HFI-BBA]$_{GBL}$ polyamide with 1,4-phenylene bis-phenylcarbamate and 4,4'-(hexafluoroisopropylidene)-bis(benzoic acid) Through Non-Isocyanate Route MPPO (0.05 g) as a CDI catalyst was added to a 250 ml three-neck flask, and γ-butyrolactone (150 ml), 1,4-phenylene bis-phenylcarbamate (3.48 g, 0.01 mole) and 4,4'-(hexafluoroisopropylidene)-bis(benzoic acid) (3.92 g, 0.01 mole) were also added. The mixed solution was mechanically stirred at 200° C. for 1 hour under a nitrogen atmosphere, and then cooled to room temperature, to obtain a precipitate. The precipitate was washed with water (1500 ml), filtered and dried to obtain 5.73 g of PA[1,4'-PPDC/HFI-BBA]$_{GBL}$ polyamide in a form of white fibers with a yield of about 96%.

The gel permeation chromatography analysis result (as shown in FIG. 2) shows that the prepared PA[1,4'-PPDC/HFI-BBA]$_{GBL}$ polyamide has a number average molecular weight (Mn) and a weight average molecular weight (Mw) of 11,200 g/mol and 26,000 g/mol, respectively. The DSC analysis result shows that Td (5%) is 492° C., and the glass transition temperature Tg is 284° C. under nitrogen atmosphere.

The properties of polyamides synthesized with isocyanate or phenyl N-phenylcarbamate are shown in Tables 3 and 4.

TABLE 3

Gel permeation chromatography analysis results of polyamides synthesized in anhydrous N-methyl-2-pyrrolidone or γ-butyrolactone polymerization solvent through aromatic carbamate route or isocyanate route

| | Gel permeation chromatography analysis results (in NMP column) | | | |
|---|---|---|---|---|
| | Mn | Mw | PD | Area % |
| PA[MDI/HFI-BBA]$_{GBL}$ | 4,400 | 11,200 | 2.5 | 93 |
| PA[4,4'-DP-MDC/HFI-BBA]$_{GBL}$ | 17,000 | 66,000 | 3.8 | 100 |
| PA[4,4'-DP-ODC/HFI-BBA]$_{GBL}$ | 15,000 | 40,400 | 2.7 | 99.3 |
| PA[1,4'-PPDC/HFI-BBA]$_{GBL}$ | 11,200 | 26,000 | 2.4 | 97 |
| PA[MDI/HFI-BBA]$_{NMP}$ | 226,800 | 845,400 | 3.7 | 24 |
| | 5,500 | 12,200 | 2.2 | 76 |
| PA[4,4'-DP-MDC/HFI-BBA]$_{NMP}$ | 35,700 | 259,800 | 7.2 | 45 |
| | 2,100 | 5,000 | 2.3 | 53 |

TABLE 4

Thermal properties of polyamides synthesized in anhydrous N-methyl-2-pyrrolidone or γ-butyrolactone polymerization solvent through aromatic carbamate route or isocyanate route

| | T5 (° C.) | T10 (° C.) | T50 (° C.) | Char Yield % | Tg (by DSC) (° C.) |
|---|---|---|---|---|---|
| PA[MDI/HFI-BBA]$_{GBL}$ | 423 | 457 | 670 | 40.2 | 272 |
| PA[4,4'-DP-MDC/HFI-BBA]$_{GBL}$ | 472 | 498 | 775 | 48.6 | 272 |
| PA[4,4'-DP-ODC/HFI-BBA]$_{GBL}$ | 440 | 482 | 560 | 0 | 270 |
| PA[1,4-PPDC/HFI-BBA]$_{GBL}$ | 492 | 526 | 723 | 45.2 | 284 |
| PA[MDI/HFI-BBA]$_{NMP}$ | 421 | 450 | 688 | 45.3 | 246 |
| PA[4,4'-DP-MDC/HFI-BBA]$_{NMP}$ | 257 | 347 | 594 | 0 | 208 |

Example 3: Effect of Polymerization Solvent

Figure 3:
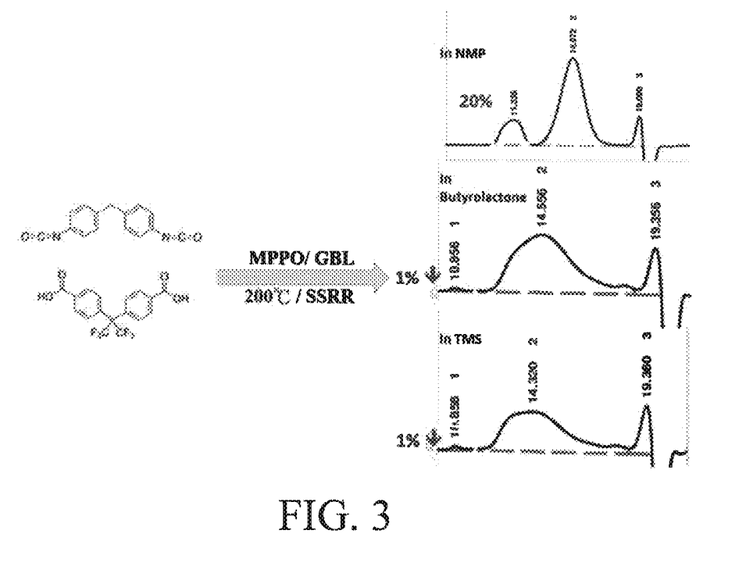
FIG. 3 shows the GPC analysis results of polyamides prepared by using a nitrogen-free polymerization solvent and a nitrogen containing polymerization solvent.
Figure 4:
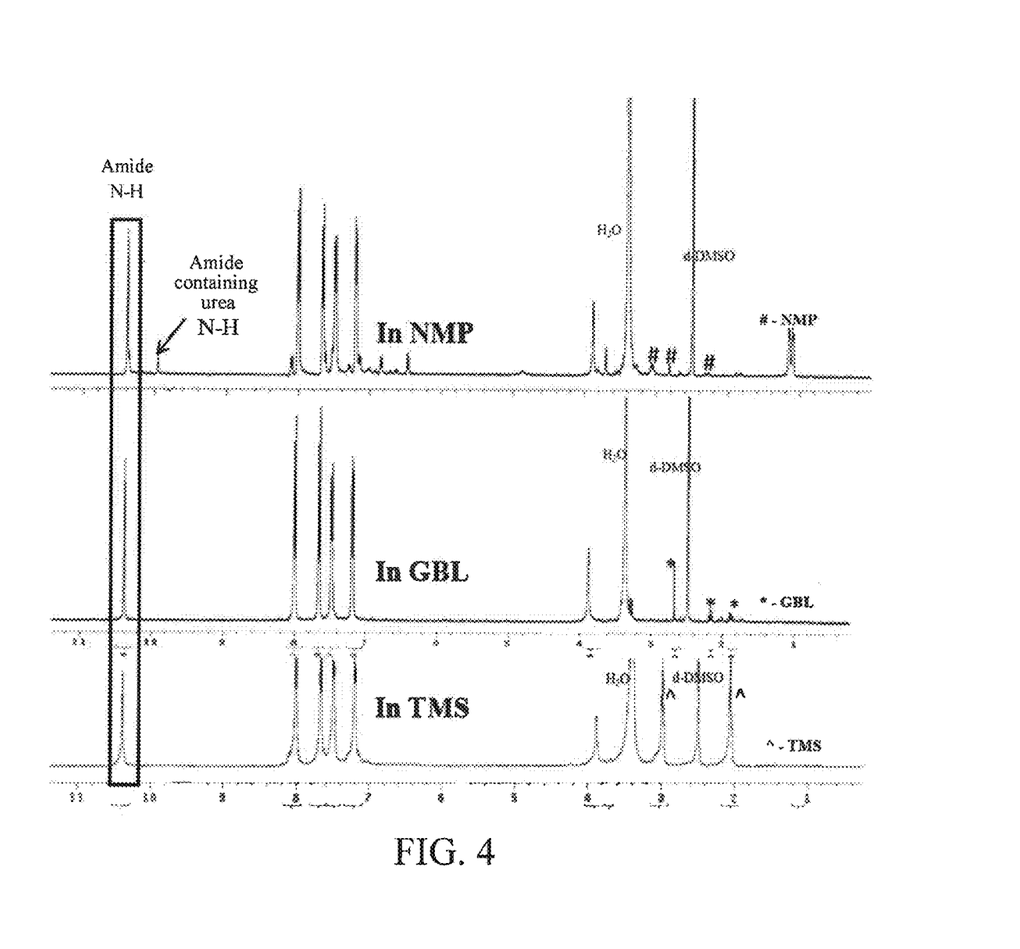
FIG. 4 shows $^1$H NMR spectra of iPr-CDI/MDI/PA polyamide prepared by using three polymerization solvents including NMP, GBL, and TMS.

When tetramethylene sulfone or γ-butyrolactone is used as a polymerization solvent in the synthesis of polyamides, the molecular weight distribution of the polyamides prepared is analyzed by gel permeation chromatography (NMP column) (FIG. 3). The result shows that the molecular weight distribution is more concentrated than the polyamides synthesized when N-methyl-2-pyrrolidone is used as a polymerization solvent, since the molecular weight distribution with a short retention time decreases from the previous 20 to 48% to 1% or less. It is found from the $^1$H NMR spectra (as shown in FIG. 4) that unlike the polyamides synthesized with N-methyl-2-pyrrolidone as a polymerization solvent, the shift of the N—H peak due to the use of tetramethylene sulfone or γ-butyrolactone as a polymerization solvent to synthesis polyamides cannot be observed in the $^1$H NMR spectra. That is, a linear polyamide of high purity was successfully synthesized by using a nitrogen-free polymerization solvent, the thermal properties of which tend to be improved compared with previous studies. The Tg of polyamides synthesized by using N-methyl-2-pyrrolidone as a polymerization solvent is only 246° C., while the Tg of polyamides synthesized by using γ-butyrolactone as a polymerization solvent can be increased to 272° C. It is believed that the thermal properties are improved because high-purity linear polyamides are synthesized by using a nitrogen-free polymerization solvent such as γ-butyrolactone.

Application Example 4: Preparation of Polyamide Film

Figure 5:
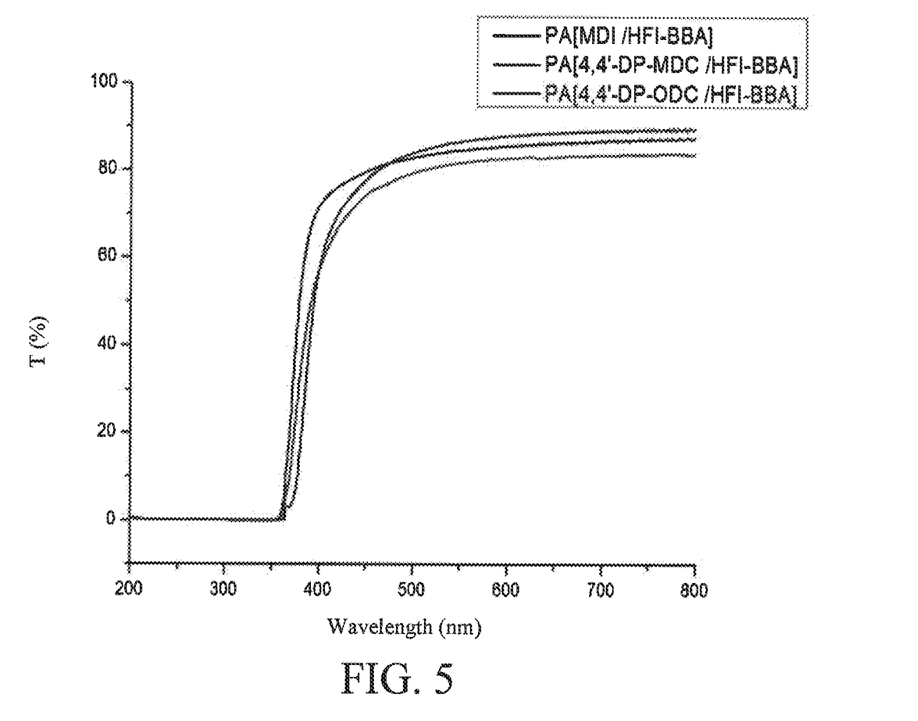
FIG. 5 shows transmittance spectra of PA[MDI/HFI-BBA]$_{GBL}$, PA[4,4'-DP-MDC/HFI-BBA]$_{GBL}$, and PA[4,4'-DP-ODC/HFI-BBA]$_{GBL}$ polyamides.
Figure 6:
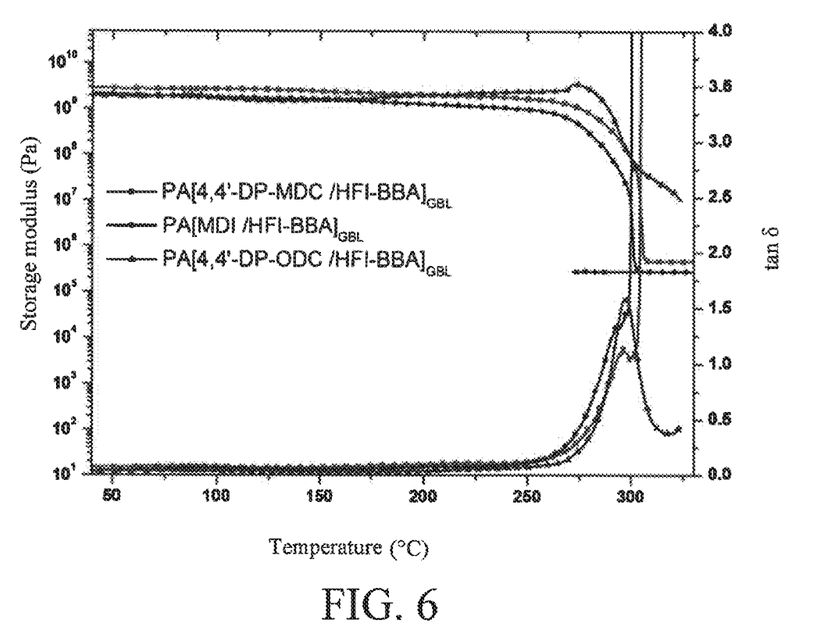
FIG. 6 shows dynamic mechanical analysis (DMA) results of PA[MDI/HFI-BBA]$_{GBL}$, PA[4,4'-DP-MDC/HFI-BBA]$_{GBL}$, and PA[4,4'-DP-ODC/HFI-BBA]$_{GBL}$.

The three polyamides PA[MDI/HFI-BBA]$_{GBL}$, PA[4,4'-DP-MDC/HFI-BBA]$_{GBL}$, and PA[4,4'-DP-ODC/HFI-BBA]$_{GBL}$ prepared in Example 2 were separately formed into films by solvent casting. The films were subjected to transmittance analysis (FIG. 5) and dynamic mechanical analysis (FIG. 6). The resulting films have an average thickness of 30 μm and appear slightly yellow. As can be seen from dynamic mechanical analysis results, the strength of film prepared from PA[4,4'-DP-MDC/HFI-BBA]$_{GBL}$ is most preferable, the E' value is up to 5400 MPa, and the glass transition temperature is 308° C. It is believed that among the three polyamides, PA[4,4'-DP-MDC/HFI-BBA]$_{GBL}$ has the highest molecular weight, and the backbone structure thereof is also more rigid than that of PA[4,4'-DP-ODC/HFI-BBA]$_{GBL}$, so it has the highest tensile strength. As mentioned above, the backbone structure of PA[4,4'-DP-ODC/HFI-BBA]$_{GBL}$ is more flexible compared with PA[4,4'-DP-MDC/HFI-BBA]$_{GBL}$ or PA[MDI/HFI-BBA]$_{GBL}$. Therefore, PA[4,4'-DP-ODC/HFI-BBA]$_{GBL}$ has the lowest tensile strength and Tg compared with the other two polyamides, but still have a tensile strength of 2400 MPa and a glass transition temperature of more than 300° C. With regard to the transmittance, since PA[4,4'-DP-ODC/HFI-BBA]$_{GBL}$ is more flexible in structure than the other two polyamides, it has the highest transmittance of 90%, followed by PA[4,4'-DP-MDC/HFI-BBA]$_{GBL}$ with a transmittance of 88% and finally the polyamide synthesized with methylene diphenyl diisocyanate with a transmittance of 84%. Compared with the polyamides in the prior art, the polyamide synthesized by using γ-butyrolactone as a polymerization solvent has quite high transparency and flexibility, and high tensile strength.

Compared with the prior art, the polyamide synthesized with the same starting materials by using N-methylpyrrolidone as a polymerization solvent has a relatively dark color and is brittle so it fails to exhibit any mechanical properties. Table 5 shows the transmittance and other test results by dynamic mechanical analysis, gel permeation chromatography, and DSC of the polyamide films prepared by the method of the present invention. The dynamic mechanical analysis results shows that there is no significant difference between PA[MDI/HFI-BBA]$_{GBL}$ and PA[4,4'-DP-MDC/HFI-BBA]$_{GBL}$ in terms of the Tg$^{(isocyanate)}$=304° C. and Tg$^{(aromatic\ carbamate)}$=308° C. However, with respect to tensile strength, PA[4,4'-DP-MDC/HFI-BBA]$_{GBL}$ has excellent mechanical and thermal properties (Td) compared with PA[MDI/HFI-BBA]$_{GBL}$. Among the polyamides prepared by the method of the present invention as described above, PA[4,4'-DP-MDC/HFI-BBA]$_{GBL}$ has desired physical properties, and is advantageous over PA[MDI/HFI-BBA]$_{GBL}$ in Td (5%) of 423° C. (isocyanate) vs 472° C. (aromatic carbamate), and in char-yield % of 40.2% (isocyanate) vs 48.6% (aromatic carbamate).

TABLE 5

Physical properties and transmittance of polyamides synthesized by using γ-butyrolactone as a polymerization solvent through aromatic carbamate route or isocyanate route

|  | Tg DMA (° C.) | E' DMA (MPa) | $T_d$ 5% (° C.) | Char yield (%) | PD | $T_{max}$ (%) | $\lambda_{min}$ (nm) |
|---|---|---|---|---|---|---|---|
| PA[MDI HFI-BBA] | 304 | 3,300 | 423 | 40.2 | 2.53 | 84 | 364 |
| PA[4,4'-DP-MDC/HFI-BBA] | 308 | 5,400 | 472 | 48.6 | 3.8 | 88 | 364 |
| PA[4,4'-DP-ODC/HFI-BBA] | 301 | 2,400 | 440 | 0 | 2.7 | 90 | 364 |
| PA[1,4-PPDC/HFI-BBA] | N/A | N/A | 492 | 45.2 | 2.4 | | |

In summary, the polyamides prepared through the non-isocyanate route of the present invention have high molecular weight and excellent physical properties, as well as high transmittance.

The above-described embodiments of the present invention are intended to be illustrative only. Numerous alternative embodiments may be devised by persons skilled in the art without departing from the scope of the following claims.

What is claimed is:

1. A method for preparing an amide or polyamide, comprising the steps of:
   (a) thermally cracking an aromatic carbamate in a polymerization solvent, to form an aromatic isocyanate solution;
   (b) subjecting the aromatic isocyanate to a self-condensation reaction in the presence of a carbodiimide (CDI) catalyst, to form an aromatic carbodiimide;
   (c) reacting the aromatic carbodiimide with a carboxylic acid, to form a reaction intermediate aromatic N-acyl urea; and
   (d) thermally cracking the aromatic N-acyl urea, to form the aromatic isocyanate and the amide or polyamide product;
   wherein Steps (b) to (d) are performed repeatedly.

2. The method according to claim 1, wherein in Steps (b) to (d), a sequential self-repetitive reaction (SSRR) is carried out.

3. The method according to claim 1, wherein the carboxylic acid is selected from the group consisting of a monocarboxylic acid, a dicarboxylic acid, and a mixture thereof.

4. The method according to claim 3, wherein the dicarboxylic acid is selected from the group consisting of an aliphatic diacid, an aromatic diacid, an aryl aliphatic diacid, and a mixture thereof.

5. The method according to claim 3, wherein the carboxylic acid is selected from the group consisting of acetic acid, benzoic acid, oxalic acid, succinic acid, adipic acid, azelaic acid, terephthalic acid, isophthalic acid, 4,4'-(hexafluoroisopropylidene)-bis(benzoic acid), and a mixture thereof.

6. The method according to claim 1, wherein the aromatic carbamate is at least one selected from the group consisting of phenyl N-phenylcarbamate (PPC), 4,4'-methylene-diphenylene bis-phenylcarbamate (4,4'-DP-MDC), 4,4'-oxy diphenylene bis-phenylcarbamate (4,4'-DP-ODC), and 1,4-phenylene bis-phenylcarbamate (1,4'-PPDC).

7. The method according to claim 1, wherein the thermal cracking in Step (a) takes place at a temperature of 120° C. or higher.

8. The method according to claim 1, wherein the CDI catalyst comprises a phosphorus-based compound, a cyclic phosphorus-based compound or a derivative thereof.

9. The method according to claim 1, wherein the CDI catalyst comprises 3-methyl-phenyl-3-phosphorene-1-oxide (MPPO).

10. The method according to claim 1, wherein Steps (b) to (d) take place at a temperature ranging from 120° C. to 300° C.

11. The method according to claim 1, wherein the polymerization solvent comprises a nitrogen-free polymerization solvent.

12. The method according to claim 11, wherein the polymerization solvent is selected from the group consisting of anhydrous tetrahydrofuran (THF), diphenyl ether (DPE), tetramethylene sulfone (TMS), and γ-butyrolactone (GBL).

13. The method according to claim 1, wherein the yield and/or purity of the prepared amide or polyamide is 85% or higher.

* * * * *